(12) United States Patent
Katz et al.

(10) Patent No.: US 10,993,705 B2
(45) Date of Patent: May 4, 2021

(54) BODY LIQUIDS COLLECTION AND DIAGNOSTIC DEVICE

(71) Applicant: NOVAMED LTD., Jerusalem (IL)

(72) Inventors: Emil Katz, Savyon (IL); Gadi Porath, Kiryat Tivon (IL)

(73) Assignee: NOVAMED LTD., Jerusalem (IL)

( * ) Notice: Subject to any disclaimer, the term of this patent is extended or adjusted under 35 U.S.C. 154(b) by 371 days.

(21) Appl. No.: 15/773,028

(22) PCT Filed: Nov. 6, 2016

(86) PCT No.: PCT/IL2016/051199
§ 371 (c)(1),
(2) Date: May 2, 2018

(87) PCT Pub. No.: WO2017/081675
PCT Pub. Date: May 18, 2017

(65) Prior Publication Data
US 2018/0325497 A1    Nov. 15, 2018

(30) Foreign Application Priority Data
Nov. 9, 2015    (IL) .......................................... 242522

(51) Int. Cl.
*A61B 10/00*    (2006.01)
*A61B 5/20*    (2006.01)
*B01L 3/00*    (2006.01)

(52) U.S. Cl.
CPC ............ *A61B 10/007* (2013.01); *A61B 5/207* (2013.01); *B01L 3/5023* (2013.01);
(Continued)

(58) Field of Classification Search
CPC ... A61B 5/207; A61B 10/007; A61B 10/0064; A61B 2010/0006; A61B 2562/0295;
(Continued)

(56) References Cited

U.S. PATENT DOCUMENTS 4,979,402 A    12/1990   Ryan et al.
5,326,707 A    7/1994    Franke et al.
(Continued)

FOREIGN PATENT DOCUMENTS

AR    069257 A4    1/2010
CN    2771863 Y    4/2006
(Continued)

OTHER PUBLICATIONS

International Search Report for PCT/12016/051199, dated Feb. 12, 2017, 4 pages.
(Continued)

*Primary Examiner* — Daniel L Cerioni
*Assistant Examiner* — Raymond P Dulman
(74) *Attorney, Agent, or Firm* — Roach Brown McCarthy & Gruber, P.C.; Kevin D. McCarthy

(57) ABSTRACT

The invention relates to a combined two-compartment device for diagnosing body liquids, which comprises: (a) an upper compartment for collecting and storing the body liquid; (b) a lower diagnostic compartment for diagnosing the body liquid at a diagnostic stage, said diagnostic compartment comprises a diagnostic strip; (c) an opening at the bottom wall between said upper compartment and said lower compartment, wherein said opening is kept blocked by a suitable valve until just before said diagnostic stage; and (d) a mechanism for releasing said blockage of said opening, thereby to allow flow of the body liquid to said lower compartment, and thereby to come into contact with said diagnostic strip and to affect the diagnostic strip accordingly.

9 Claims, 14 Drawing Sheets

(52) U.S. Cl.
CPC ... *A61B 10/0064* (2013.01); *A61B 2010/0006* (2013.01); *A61B 2562/0295* (2013.01); *B01L 2200/026* (2013.01); *B01L 2200/0605* (2013.01); *B01L 2200/0621* (2013.01); *B01L 2300/047* (2013.01); *B01L 2300/049* (2013.01); *B01L 2300/0672* (2013.01); *B01L 2300/0681* (2013.01); *B01L 2300/087* (2013.01); *B01L 2300/0832* (2013.01)

(58) Field of Classification Search
CPC ............. B01L 3/5023; B01L 2200/026; B01L 2200/0605; B01L 2200/0621; B01L 2300/047; B01L 2300/049; B01L 2300/0672
See application file for complete search history.

(56) References Cited

U.S. PATENT DOCUMENTS

| | | | |
|---|---|---|---|
| 5,441,894 A * | 8/1995 | Coleman | G01N 33/54366 436/518 |
| 6,277,646 B1 | 8/2001 | Guirguis et al. | |
| 6,508,987 B1 | 1/2003 | Wilkinson et al. | |
| 7,029,627 B2 | 4/2006 | Alley | |
| 7,758,815 B2 | 7/2010 | Hartselle | |
| 7,981,382 B2 | 7/2011 | Wong | |
| 8,163,253 B1 | 4/2012 | Hartselle | |
| 8,486,353 B2 | 7/2013 | Wu | |
| 2002/0009389 A1 | 1/2002 | Lappe | |
| 2002/0042145 A1 * | 4/2002 | Forsberg | G01N 33/54366 436/165 |
| 2002/0048819 A1 | 4/2002 | Alley | |
| 2002/0081233 A1 | 6/2002 | Lappe et al. | |
| 2002/0085953 A1 | 7/2002 | Parker | |
| 2003/0099572 A1 | 5/2003 | Ng et al. | |
| 2003/0129088 A1 | 7/2003 | Lee | |
| 2003/0206829 A1 | 11/2003 | Cui | |
| 2004/0060374 A1 | 4/2004 | Goodin | |
| 2004/0197228 A1 | 10/2004 | Tydings | |
| 2005/0048670 A1 | 3/2005 | Wu et al. | |
| 2005/0112024 A1 | 5/2005 | Guo et al. | |
| 2007/0025886 A1 * | 2/2007 | Yong | B01L 3/502 422/400 |
| 2007/0065339 A1 | 3/2007 | Huff | |
| 2007/0092402 A1 * | 4/2007 | Wu | B01L 3/502 422/400 |
| 2008/0019867 A1 | 1/2008 | Johnson | |
| 2009/0004058 A1 | 1/2009 | Liang et al. | |
| 2011/0107824 A1 * | 5/2011 | Lv | B01L 3/5023 73/64.56 |
| 2011/0287434 A1 | 11/2011 | Menon-Johansson | |
| 2012/0142020 A1 * | 6/2012 | Miller | G01N 1/38 435/7.1 |
| 2012/0164751 A1 * | 6/2012 | Liang | B01L 3/502 436/501 |
| 2013/0164190 A1 | 6/2013 | Plante | |
| 2013/0175266 A1 | 7/2013 | Ellis | |
| 2013/0209326 A1 * | 8/2013 | Williams | B01L 3/5027 422/502 |
| 2014/0271367 A1 | 9/2014 | Wong | |
| 2015/0140681 A1 * | 5/2015 | Meng | B01L 9/00 436/501 |
| 2015/0185240 A1 * | 7/2015 | Dai | A61B 10/0045 422/68.1 |
| 2017/0036204 A1 | 2/2017 | Zercher et al. | |

FOREIGN PATENT DOCUMENTS

| | | |
|---|---|---|
| CN | 1882831 A | 12/2006 |
| CN | 101598724 A | 12/2009 |
| CN | 203164183 U | 8/2013 |
| CN | 203732320 U | 7/2014 |
| CN | 203929775 U | 11/2014 |
| CN | 204228475 U | 3/2015 |
| CN | 104955402 A | 9/2015 |
| WO | 2007/058461 A1 | 5/2007 |

OTHER PUBLICATIONS

Written Opinion of the International Searching Authority for PCT/IL2016/051199, dated Feb. 12, 2017, 8 pages.
Corrected version of the International Preliminary Report on Patentability for PCT/IL2016/051199, dated May 2, 2018, 10 pages.
Chinese language office action for Chinese Application No201680074079.X dated Aug. 5, 2019 (6 pages) and rresponding search report (3 pages).
Communication and Supplementary European Search Report for EP 16 86 3777—a counterpart foreign application—dated May 21, 2019 (8 pages).
Ohno, Akemi. (2014). [Evolution of urine test paper]. Rinsho byori. The Japanese journal of clinical pathology. 62. 668-73. https ://ores. su/en/j ournals/rinsho-byori+he-j apane se-j ournal-of- clinical-pathology/.
Daka, Joseph N., et al. "Laboratory evaluation of a SpectraMax microplate reader and test strips for field measurement of creatinine in spot urine samples in the event of a radiological accident." Health physics 101.2 (2011): 154-158. https://insights.ovid.com/article/00004032-201108000-00009.
A E Burkhardt et al., "A reagent strip for measuring the specific gravity of urine" Clinical Chemistry, vol. 28, Issue 10, Oct. 1, 1982, pp. 2068-2072, https://doi.org/10.1093/clinchem/28.10.2068.
Office action from a corresponding Russian application No. 2018121343 that was transmitted on Jan. 30, 2020 (8 pages) and English translation (3 pages).
Office action from the Japanese Patent Office regarding corresponding Japanese Patent Application No. 2018-543474 transmitted on Oct. 6, 2020 (6 pages—with an English translation 5 pages)—this IDS cites the corresponding English language US patent documents of the cited Japanese and PCT patent documents.

* cited by examiner

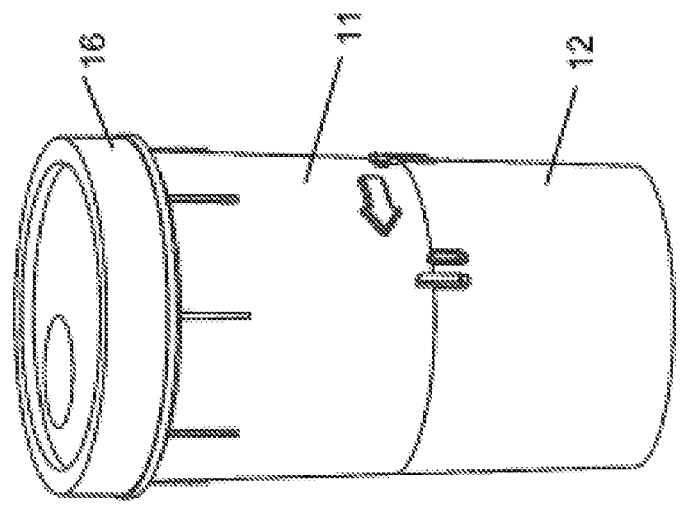
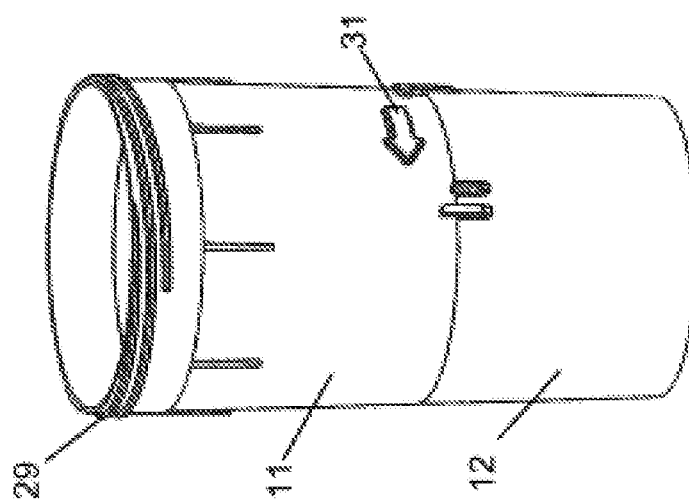
Fig. 1a
Fig. 1b

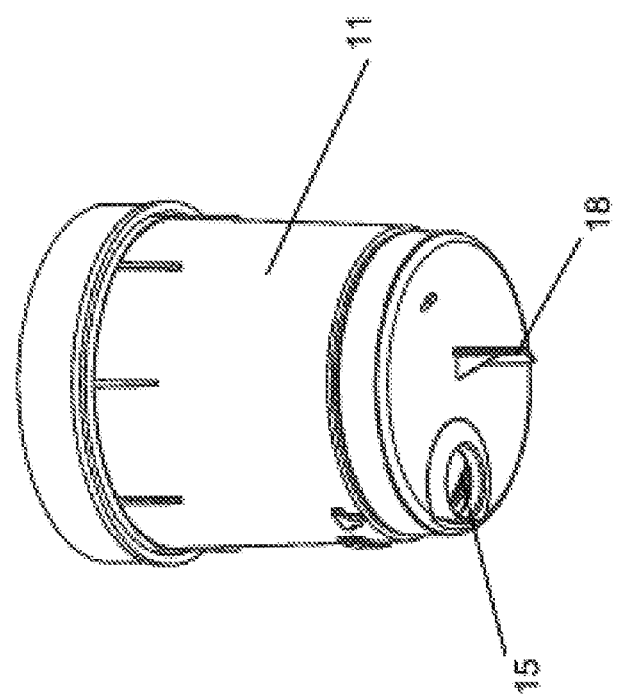

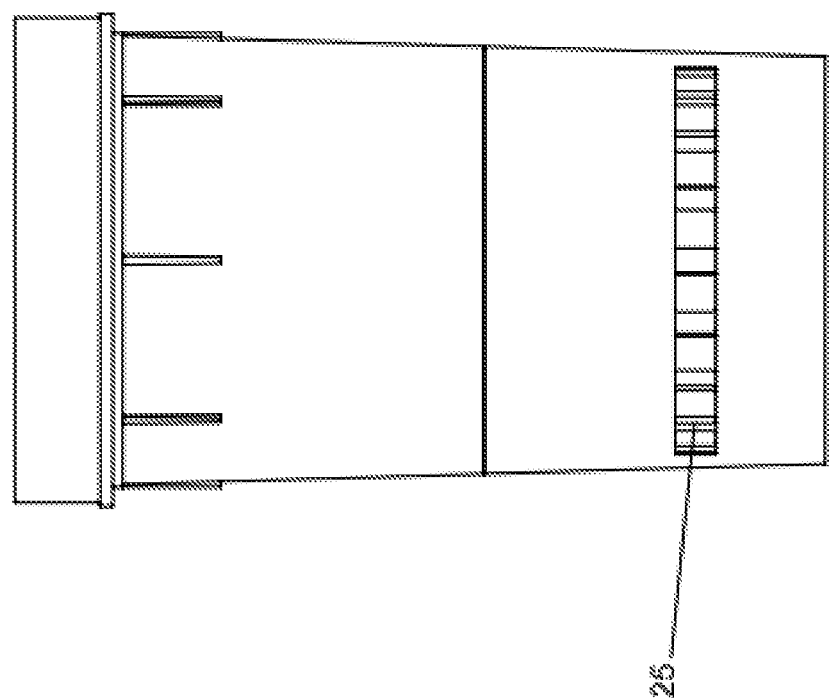

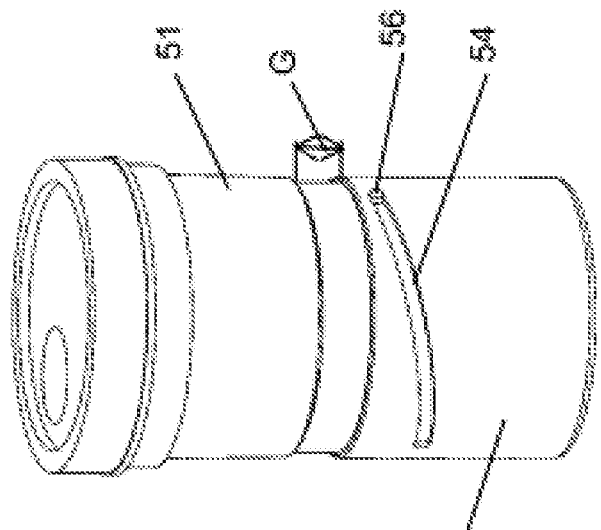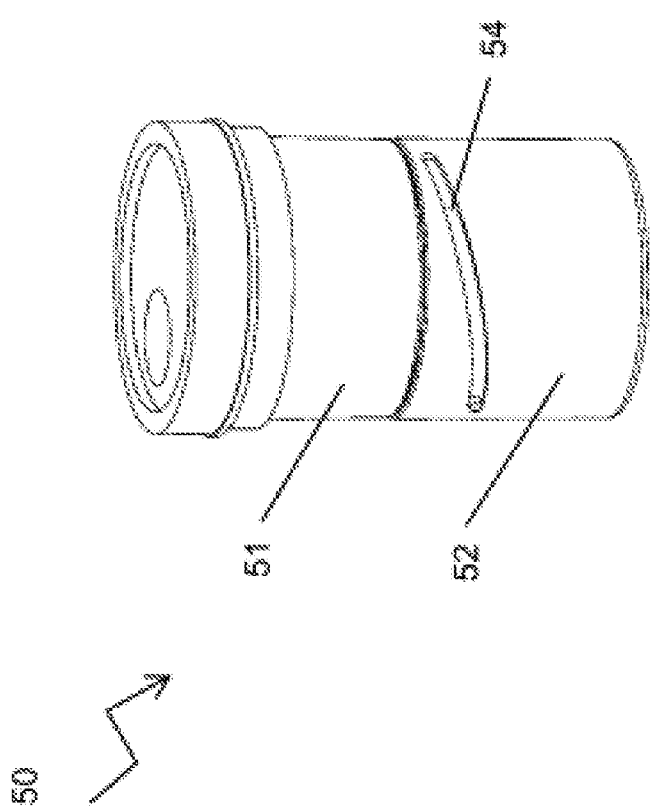

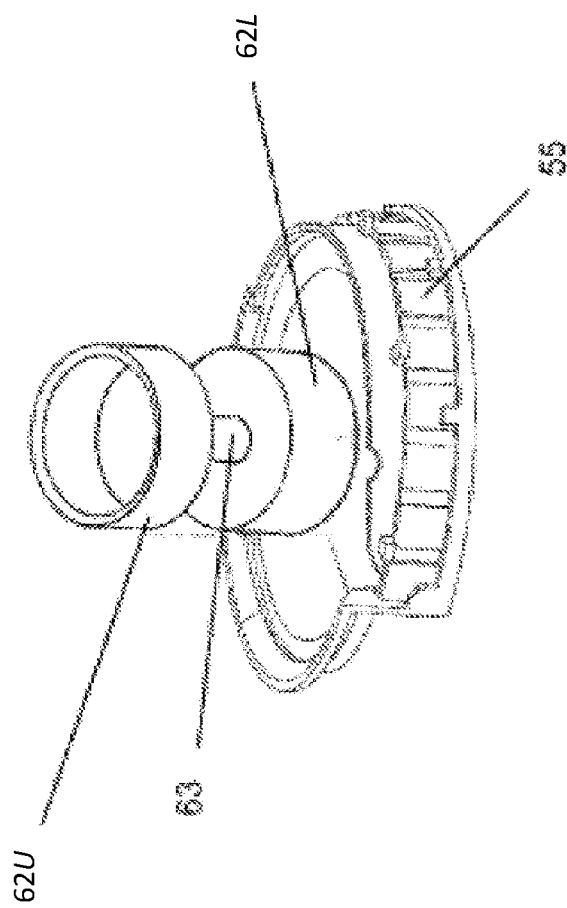

BODY LIQUIDS COLLECTION AND DIAGNOSTIC DEVICE

FIELD OF THE INVENTION

The present invention relates in general to medical and laboratory devices for diagnosing body liquids. More specifically, the invention mainly relates to a two-compartment device for diagnosing urine or other body liquids.

BACKGROUND OF THE INVENTION

Various body liquids such as blood, urine, sweat, water, waste, food, etc., are valuable sources for diagnosing and determining health problems, or for the early detection of symptoms that may develop to significant health problems. While the device of the present invention is particularly useful for collecting and diagnosing urine, and while the following description is focused on said particular object, this should not be construed as a limitation, as the same device may similarly be used for testing other body liquids, with or without the simple adaptations to the device.

Using the currently available urine diagnostic device, the patient typically urinates into a urine cup, covers it by a suitable lid, and submits it to medical staff for the performance of laboratory diagnostics. Generally in the laboratory, a laboratory assistant typically opens the lid, and immerses one or more of dedicated diagnostic reagent sticks in the urine sample. Each of the diagnostic sticks is covered at least partially by one or more of specific material layers that react to the specific composition of the urine. In one typical example, the material layer changes its color based on the specific composition of the urine. In some similar cases, one stick may comprise plurality of diagnostic layers, for separately diagnosing various characteristics, materials or compositions of the urine. The results are then used as a preliminary diagnostic tool for the physicians to determine the health condition of the patient.

In many cases the "first urine in the morning" is preferably required for the urine diagnosis, and for that purpose the patient needs to bring a cup filled with urine, from his home to the medical center, or alternatively to urinate into the cup at the medical center. The actual diagnosis procedure must be performed within no more than several hours from the urination time. Furthermore, the maximal period from the time of exposure of the diagnostic stick to the urine and until the time of its inspection should not exceed more than a few minutes. In order to perform the procedure above, a laboratory assistant or nurse has to open the lid of the cup, and to operate in a non-sterilized and unpleasant manner, namely dipping the diagnostic stick into the open cup.

In still another prior art arrangement, a dedicated cover lid with a test tube is applied to the cup before the diagnosis, and a sample from the urine is sucked into the test tube. Then, the urine content of the tube or a portion thereof is spilled over a diagnostic stick or the stick is immersed in the liquid, and the results are obtained in a similar manner as described above.

The existing urine diagnostic devices and procedures possess several inherent drawbacks as follows:
  i. The diagnostic cup procedure is associated with hygienic and urine contaminations, that endangers the medical staff, and the public. It is desirable to provide a procedure and device which eliminates the need for the staff at a clinic or Lab to dip a manual strip into an open urine cup.
  ii. As also noted above, the period during which the diagnostic stick is immersed in the urine and until inspection of the stick must be made is short and should not exceed a few minutes. It is desirable to extend this period.

Current devices for diagnosing urine are in general cumbersome and unpleasant to the staff. It is therefore highly desired to provide a device which is of low cost, and is simple to operate by both a patient (at his home or elsewhere) and by the medical assistant and operated automatically by the staff.

It is an object of the invention to provide a device which operates in a more hygienic conditions relative to the prior art devices.

It is still another object of the invention to extend the short period during which the stick can be immersed in the urine, and until an inspection must be made.

Other objects and advantages of the present invention will become apparent as the description proceeds.

SUMMARY OF THE INVENTION

The invention relates to a combined two-compartment device for diagnosing body liquids, which comprises: (a) an upper compartment for collecting and storing the body liquid; (b) a lower diagnostic compartment for diagnosing the body liquid at a diagnostic stage, said diagnostic compartment comprises a diagnostic strip; (c) an opening at the bottom wall between said upper compartment and said lower compartment, wherein said opening is kept blocked by a suitable valve until just before said diagnostic stage; and (d) a mechanism for releasing said blockage of said opening, thereby to allow flow of the body liquid to said lower compartment, and thereby to come into contact with said diagnostic strip and to affect the diagnostic strip accordingly.

In an embodiment of the invention, the body liquid is urine.

In an embodiment of the invention, the wall of said lower compartment is at least partially transparent, thereby to allow visual inspection of color alterations within the diagnostic strip.

In an embodiment of the invention, said diagnostic strip comprises one or more sections, each being coated by a different material layer respectively, and each said layers reacts differently to a specific material or composition of the body liquid, respectively.

In an embodiment of the invention, said blockage of the opening is caused by one or more valves between the upper and the lower compartments.

In an embodiment of the invention, each of the valves has a protrusion shape or a piston valve.

In an embodiment of the invention, during blockage, the relevant valve is elastically forced against the opening.

In an embodiment of the invention, said blockage is released by causing a relative rotation between the lower compartment and the upper compartment, thereby removing the valve from the opening.

In an embodiment of the invention, said relative rotation between said upper compartment and said lower compartment defines a limited period of an "open valve state" between two "closed-valve states", thereby defining a dosage volume of the body liquid which flows into said lower compartment during said "open valve state".

In an embodiment of the invention, said relative rotation is limited by either one or more stoppers, or by a limiting slot.

In an embodiment of the invention, the flow of the body liquid into the lower compartment is caused as a result of a gravitational force.

In an embodiment of the invention, the dosage volume is pre-determined by an opening dimension or opening period of the flow between the two compartments.

In an embodiment of the invention, said dosage predetermination is made by a distance between two valves.

In an embodiment of the invention, the device comprises an absorbing element at the lower compartment for absorbing the body liquid after some specific period during which the liquid was in contact with the diagnostic strip.

In an embodiment of the invention, said diagnostic strip at the lower compartment is either vertical or horizontal.

In an embodiment of the invention, the device has a substantially cylindrical shape.

In an embodiment of the invention, a portion of the lower compartment is partially flat, to enable reading of the diagnostic strip by means of a scanner.

In an embodiment of the invention, the device further comprising means at the upper compartment for removing a body liquid dosage into an Evacuated Test Tube or to another test device, without opening the a cover of the device.

In an embodiment of the invention, said upper compartment is a temporary compartment, wherein the device further comprising a main compartment and a valve, wherein during a pre-diagnostic stage said valve seals a liquid passage opening between said temporary compartment and said diagnostic compartment, while opening a liquid passage between said main compartment and said temporary compartment, and wherein during a diagnostic stage said valve is moved thereby to open said passage between the temporary compartment and said diagnostic compartment, while sealing the opening between said main compartment and said temporary compartment.

In an embodiment of the invention, said temporary compartment comprises a relatively small amount of liquid sufficient to affect said diagnostic strip.

In an embodiment of the invention, the device further comprising a bottom compartment, wherein a rate of flow between said diagnostic compartment and said bottom compartment is regulated by means of a flow regulator.

In an embodiment of the invention, said flow regulator is a small diameter opening, a filter, an open cells sponge, or a float.

BRIEF DESCRIPTION OF THE DRAWINGS

In the drawings:

FIGS. 1a and 1b show the general structure of a urine collection and diagnostic device, according to one embodiment of the present invention;

FIG. 2a-2d shows the internal structure of the device, according to an embodiment of the invention;

FIG. 3a shows the general view of the device, with a diagnostic strip having a plurality of sections, while the strip is disposed over a circular surface;

FIGS. 5a and 5b show a second embodiment of the device of the invention, having a slanted guiding slot for a bayonet type engagement between the upper portion and the lower portion of the device;

FIGS. 6a-6d show a more detailed structure of the device according to the second embodiment of the invention.

DETAILED DESCRIPTION OF PREFERRED EMBODIMENTS

Figure 2B:
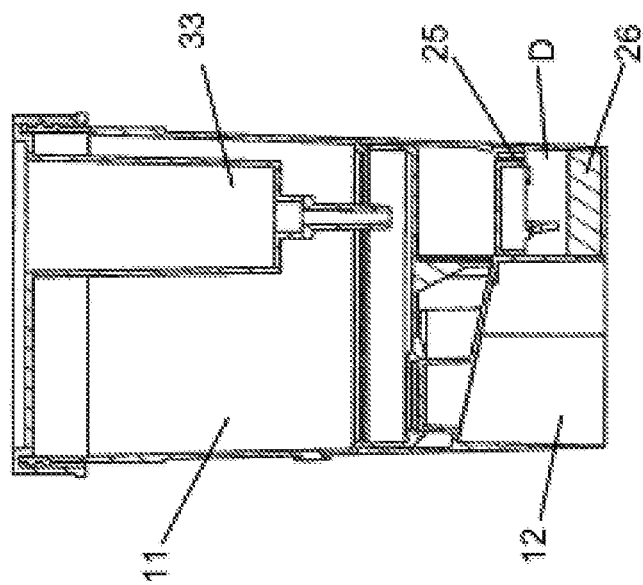

The present invention relates to a urine collection and diagnostic device, which mainly comprises two separate compartments: (a) a urine collection compartment; and (b) a urine diagnostic compartment. As will be further discussed, the functions of the urine collection and the urine diagnosis are both performed within the same device of the invention.

FIG. 1a shows the general structure of a urine collection and diagnostic device 10, according to one embodiment of the present invention, and FIG. 1b shows the same device with the lid removed. The device 10 comprises an upper collection compartment 11, and a lower diagnostic compartment 12. As will be further explained below, the two compartments 11 and 12 are separated in terms of liquid flow, as long as the diagnosis is not performed. During urination, the urine is accumulated within the upper compartment 11, and is kept there until the time of diagnosis. Although not visible from FIG. 1, the outer wall of the bottom compartment 12 is at least partially transparent, and it comprises a urine diagnostic strip, which in turn comprises one or more diagnostic sections, each covered by a different layer or composition of layers, similar to those existing in one or more of the diagnostic sticks of the prior art. The diagnostic strip, particularly the various diagnostic sections of the strip, can be seen by the medical assistant via the transparent wall of the lower compartment 12, thereby any change of color or view of the section due to contact with the urine can be easily seen by the assistant. Arrow 31 indicates the direction of which the upper compartment should be rotated relative to the lower compartment in order to initiate the diagnostic stage.

As also mentioned, the urine is contained within the upper compartment 11 until just before the diagnostic procedure. For that purpose, lid 16 is provided to cover the cup after urination, for example, and it is engaged with the compartment 11 by means of thread 29, therefore to keep the urine in hygienic conditions. In order to initiate the diagnostic procedure, the assistant performs an action which opens an opening (which was previously blocked) at the dividing wall between the upper and lower compartments, 11 and 12 respectively, such that at least a portion of the urine within the upper compartment 11 flows to within the lower compartment 12, and comes into contact with the various sections of the diagnostic strip. The responses of the various sections (such as their change of color) are then analyzed to provide the diagnostic results in a manner known in the art.

Figure 4:
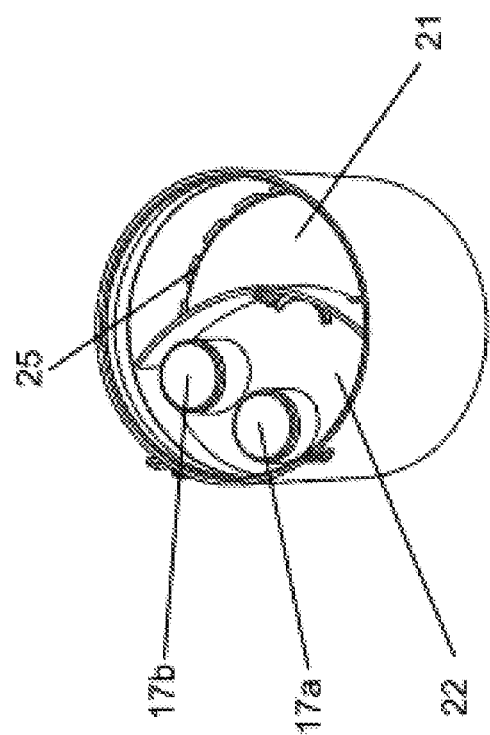
FIG. 4 shows the general structure of the lower compartment.
Figure 6A:
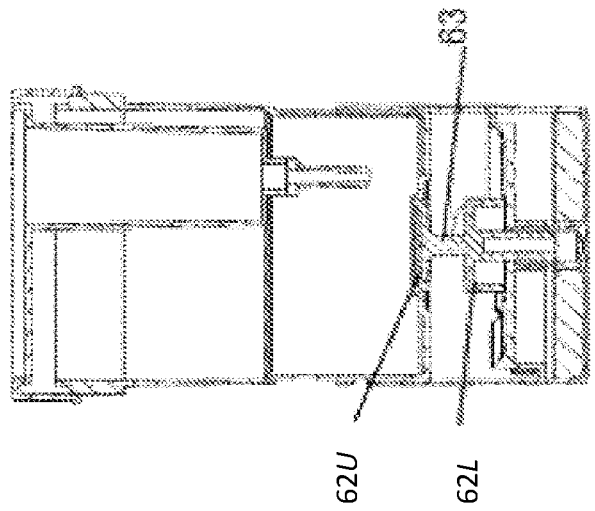
Figure 6B:
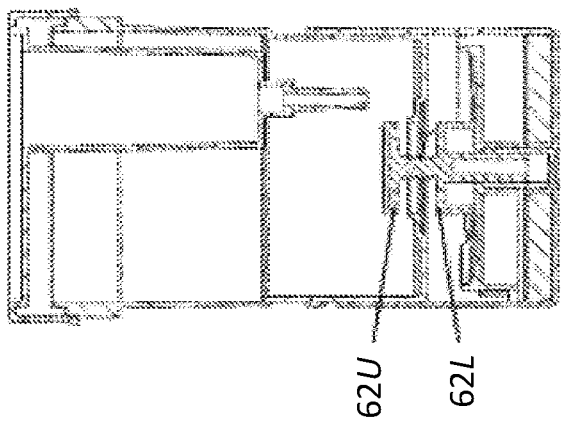
Figure 6C:
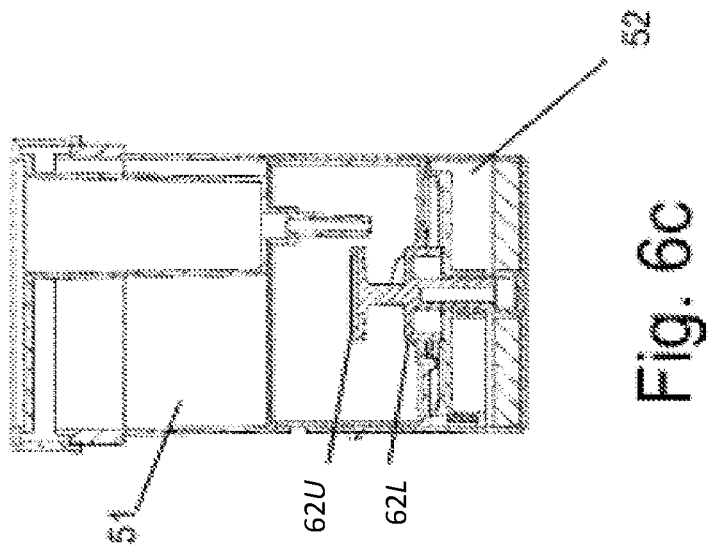

FIG. 2a shows in perspective view the structure of the upper compartment 11, according to an embodiment of the invention. FIG. 2b is a cross-sectional view of the upper and lower compartments. FIG. 4 shows the general structure of the upper portion of the lower compartment.

In an embodiment of the invention, the lower compartment 12 is attached to the upper compartment 11 by a stationary portion 21 (i.e., a portion which remains stationary with respect to the upper compartment), while the bottom compartment 12 further comprises a rotational mechanism 22 (i.e., a portion which is rotatable with respect to the upper compartment and the stationary portion 21) which is attached to the outer wall of the compartment 12. More specifically, lower compartment 12 comprises a rotational mechanism 22, which initially blocks the passage of urine from the upper compartment 11 to the lower compartment 12, and only when it is desired to initiate the diagnosis, this liquid passage is temporarily opened to allow the flow of a dosage of urine from the upper compartment 11 to the lower compartment 12. In one embodiment, the opening 15 between the upper compartment 11 and the lower compartment 12 is blocked by means of valve (protrusion) 17a, which is elastically forced against said opening. The additional protrusion 17b is inactive, as it is not positioned against any opening. In order to initiate the diagnostic, a limited angular rotation is performed between the outer wall of the lower compartment and the outer wall of the upper compartment, such that the first protrusion 17a leaves its previous position against opening 15, and the second protrusion 17b is elastically forced against the opening 15, to again block the passage of urine from the upper compartment 11 to the lower compartment 12. A flow of urine therefore takes place during an opening time T, i.e., between an earlier blockage by protrusion 17a, and a later blockage by protrusion 17b. Typically, during time T a specific dosage D of urine flows to within the lower compartment 12, as shown in FIG. 2b. Therefore, the dosage volume is in fact proportional to the distance between protrusions 17a and 17b. A stoppage protrusion 18 at the bottom surface of the upper compartment 11 is used to limit the angular displacement to a specific maximal rotation angle, for example, 25°.

Figure 2D:
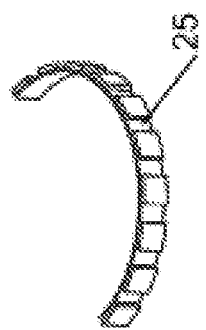
Figure 2C:
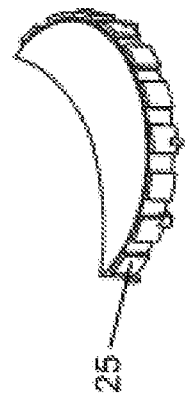

In one embodiment, dosage D fills the lower compartment 12 with about 7 mm height of urine, which is sufficient to affect the various sections of strip 25 (shown in FIGS. 4, 2c, and 2d), which are in turn visible from the exterior of the transparent wall of the lower compartment 12. The dosage D comes into contact with the strip 25 for a limited time t, until the urine dosage is fully absorbed within sponge 26 at the bottom of the lower compartment 12. Therefore, in fact after the elapse of the period t, the strip 25 is no longer immersed with urine, therefore the indication can remain reliable and visible for a relatively long period, a period which is longer compared to the period in the prior art procedures where the indication from the diagnostic stick must be taken within a maximal period of several minutes from the time of immersing of the stick in the urine.

In still another embodiment shown in the cross-sectional view of FIG. 2b, the upper compartment 11 comprises a suction compartment 33 for the introduction of a suction tube. More specifically, when necessary to have an additional urine sample for diagnostic outside of the cup, a vacuum based suction pump (not shown) within compartment 33 may be used for this purpose.

Figure 3B:
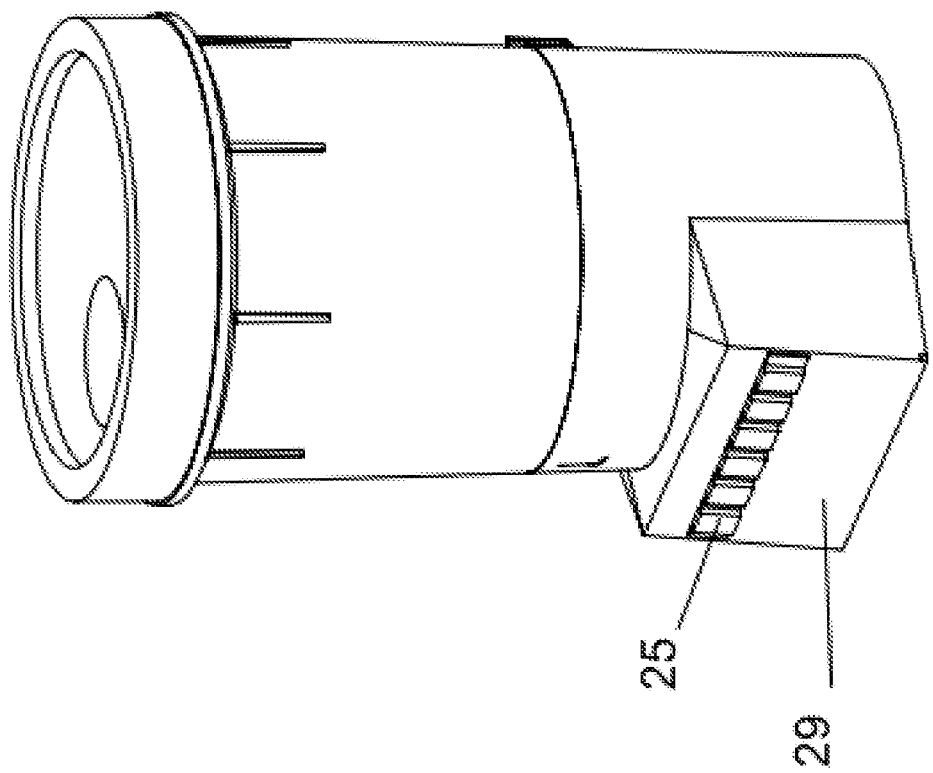
FIG. 3b shows the general view of the device, with a diagnostic strip having a plurality of sections, while the strip is disposed over a flat surface.

FIGS. 3a and 3b shows two manners by which the diagnostic layers are disposed within the device of the invention. In the device of FIG. 3a, the diagnostic strip 25 is disposed internally within compartment 12, however over a circular internal surface of the compartment. In the device of FIG. 3b, the diagnostic strip 25 is disposed internally within compartment 12, however over a flat internal surface of the compartment. As shown, the internal flat surface 29 is located, for example on an extension from the circular wall of compartment 12. The use of a flat surface is in some cases advantageous, as it enables reading of the strip results by an automatic scanner FIGS. 5a and 5b show still another embodiment of the device of the invention. In this embodiment, the device 50 comprises a slanted guiding slot 54 and a rigid bayonet button 56 which is always maintained within the slot 54. Therefore, relative rotation between the upper compartment 51 and the lower compartment 52 in fact causes the elevation of the upper compartment 51 with respect to the lower compartment 52, forming a gap G between said two compartments. FIG. 5b shows the device while the upper compartment 51 is in its elevated state (relative to the lower compartment 52), therefore the gap G is clearly seen. Therefore, the device in fact has two states, an "elevated state" (as shown in FIG. 5b) and a "normal state" as in FIG. 5a. In addition, and as shown in FIGS. 6a-6d, the device further comprises a double-valve unit 61, having an upper valve 62u, and a lower valve 62l. The two valves 62u and 62l are coaxial, and they are connected by a central rod 63. As shown, the two valves 62u and 62l are spaced apart one another. The upper valve 62u is attached to a surface of the upper compartment 51, such that it is elevated by the upper compartment when the upper compartment is rotated with respect to the lower compartment 52. More specifically, the two valves are arranged such that when the device is in its "normal state" (see FIG. 6a), the opening 65 is blocked by the upper valve 62u, and while the device is in its "elevated state" (see FIG. 6c), the opening 65 is blocked by the lower valve 62l. Anywhere in between said two valves (see FIG. 6b), the passage between the upper compartment 51 and the lower compartment 52 is in fact open (due to the shorter diameter of rod 63 relative to the diameter of the valves 62u and 62l, respectively), such that urine may flow from the upper compartment to the lower compartment. Normally, the opening period of the passage is relatively short it is defined by the transfer time between the closure by the upper valve until closure by the lower valve), and it is designed to allow a dosage of a specific volume of urine to flow to the lower compartment. The rest of the elements of the device 50 are essentially the same as those of device 10 (for example, diagnostic layers 55 are substantially equivalent to diagnostic layers 25 of the first embodiment), therefore they will not be described herein in detail.

In still another embodiment, the two-compartment device 10 of the invention may also be used for alcohol and drug tests. As known, alcohol and drug tests must be initiated shortly after the urination, to ensure the reliability of the test results. For this purpose, the urine temperature is checked to ensure that the temperature of the urine is in fact close enough to the body temperature. Therefore, for drug and alcohol tests, the two-compartment device of the invention may further comprise a thermostat (not shown). Moreover, when using a conventional diagnostic stick to test drugs, only the lower portion of the stick is immersed in the urine, while the urine permeates and "climbs" the stick upon absorption. In order to conform to this characteristic of said procedure of the prior art, the strip (25 or 55 respectively), may be mounted within the lower compartment 12 in a vertical orientation.

Figure 7A:
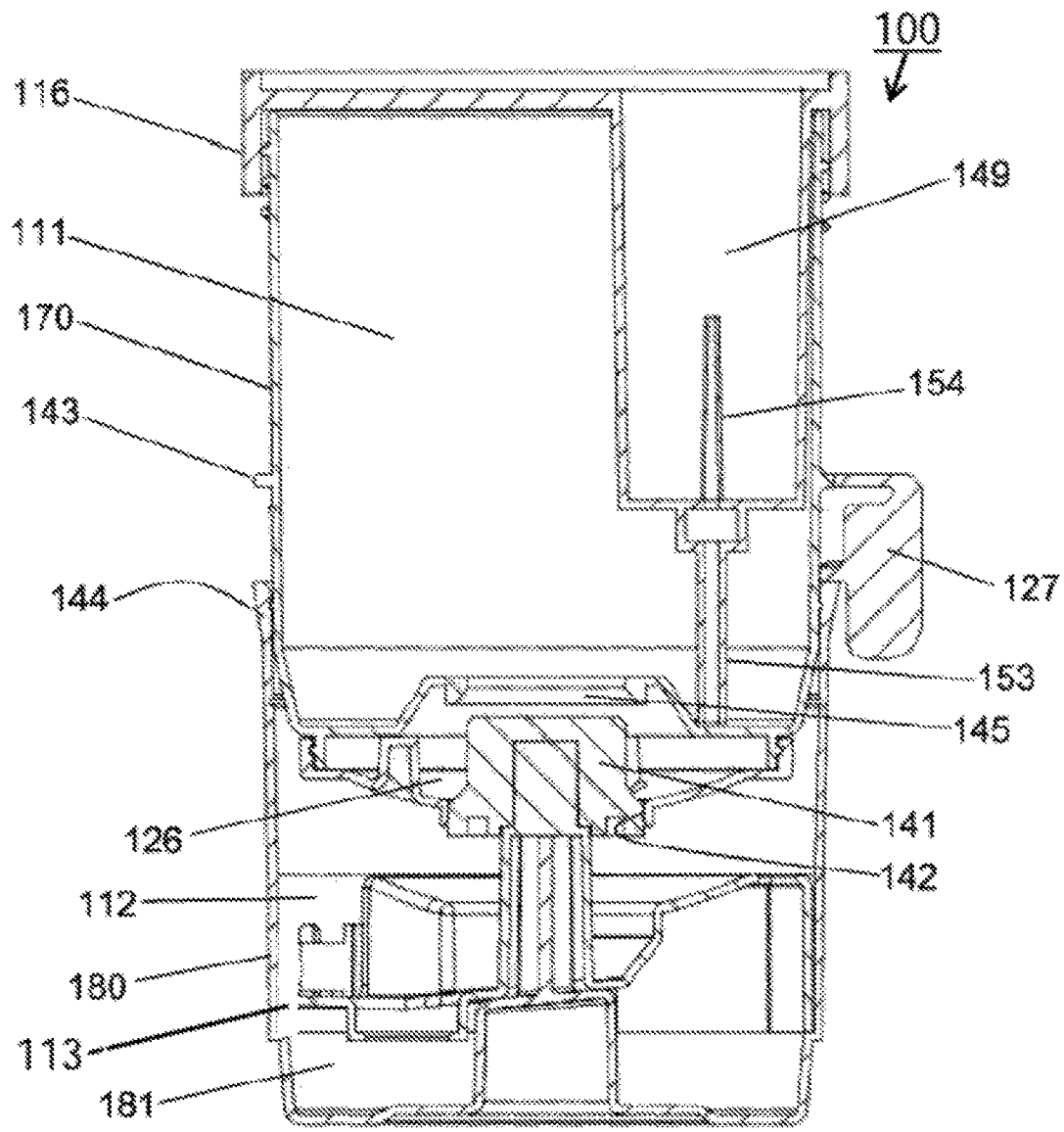
FIGS. 7a to 7d shows a structure of the device according to a third embodiment of the invention.
Figure 7B:
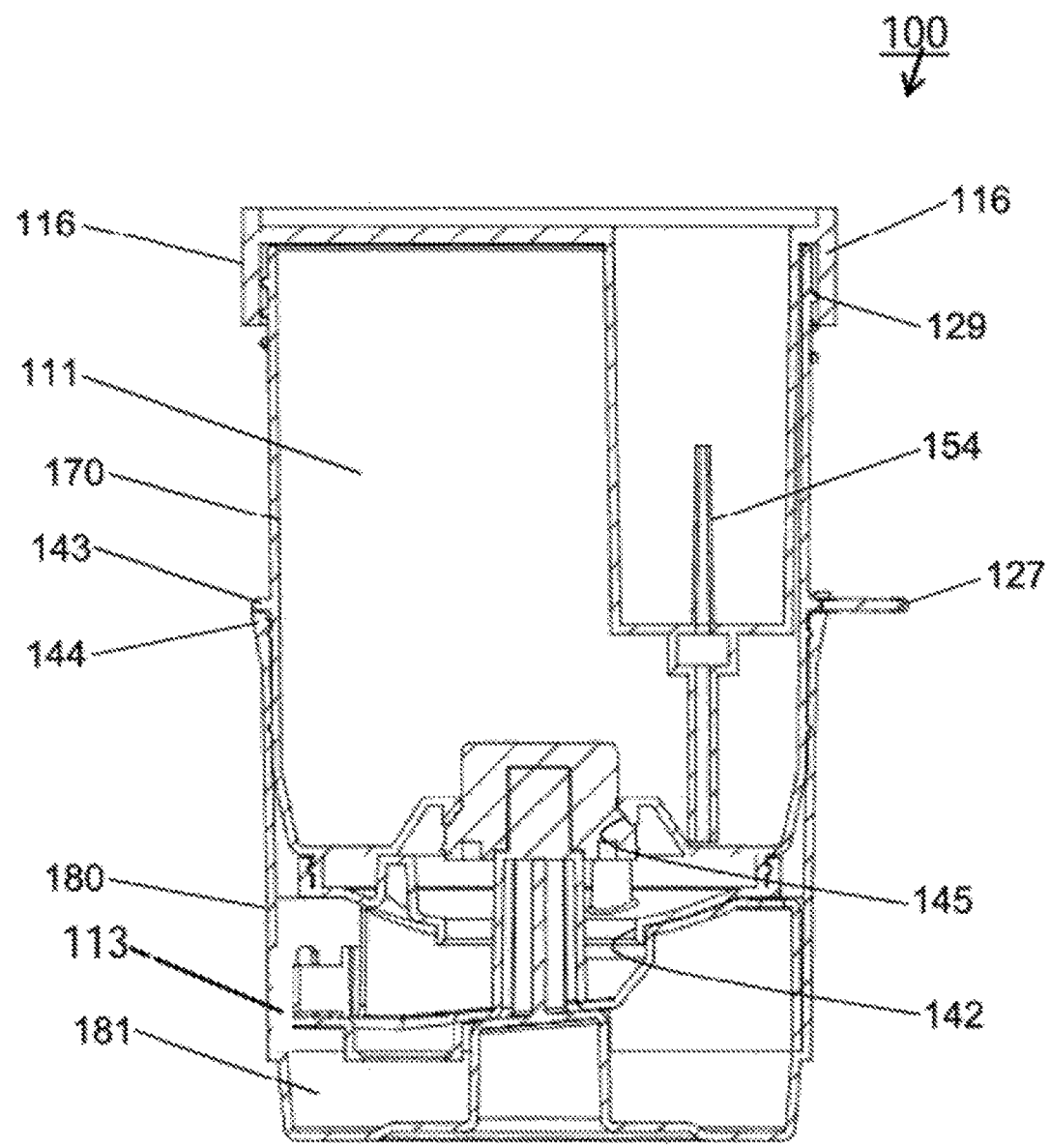
Figure 7C:
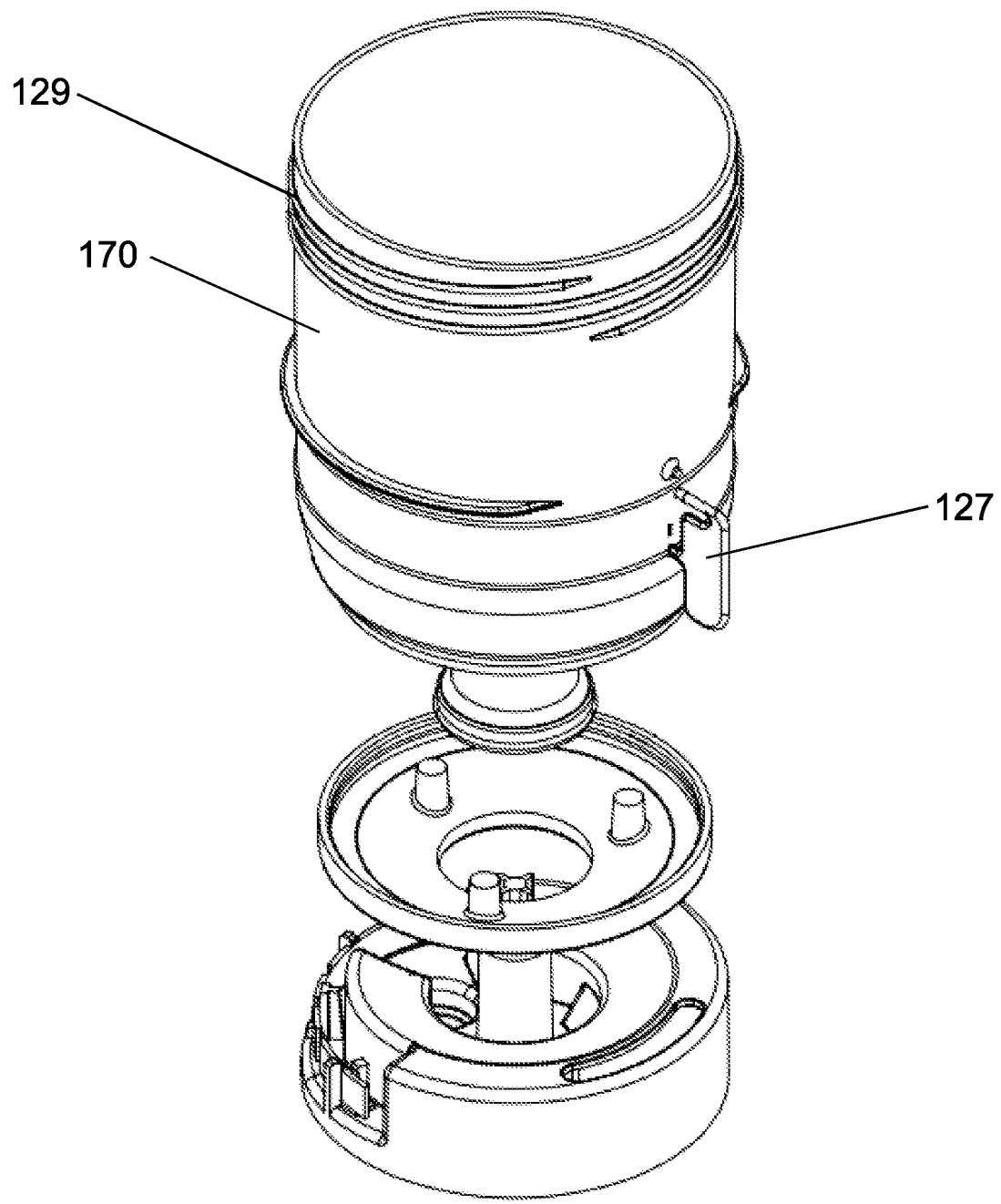

FIGS. 7a to 7d show a urine collection and diagnostic device 100 according to a third embodiment of the invention. FIG. 7a shows the general structure of the device 100 in its collection and pre-diagnostic stage, and FIG. 7b shows the same device in its diagnostic stage. The device 100 mainly comprises three portions as follows:
(a) A lower portion 180;
(b) An upper portion 170 which is vertically slidable with respect to the lower portion; and
(c) A lid portion 116 which covers the upper portion of the device (and optionally enables hygienic removal of urine by means of a syringe).

The upper portion 170 comprises an upper main compartment 111 and a temporary compartment 126. The lower portion comprises a lower diagnostic compartment 112, where the one or more diagnostic strips are located. During the first stage of collection and pre-diagnostic, the urine is maintained within the main compartment 111 (which contains typically up to 70-100 milliliter of liquid) and within the temporary compartment 126 (which typically contains about milliliter of liquid 9-10 milliliter), both said compartments are in free flow connection at this stage. The upper compartments 111 and 126 are separated in terms of liquid flow from the lower compartment 112, as long as the diagnostic stage has not been initiated. During urination, the urine is accumulated within the upper compartments 111 and 126, and is kept there until the time of diagnosis. Although not visible from FIGS. 7a and 7b, the outer wall of the bottom compartment 112 is at least partially transparent, and it comprises a urine diagnostic strip, which in turn comprises one or more diagnostic sections, each covered by a different layer or composition of layers. The diagnostic strip, particularly the various diagnostic sections of the strip, can be seen by the medical assistant via the transparent wall of the lower compartment 112, thereby any change of color or view of the section due to contact with the urine can be easily seen by the assistant.

Lid 116 is provided to cover the cup after urination, and it is engaged with the upper portion 170 by means of thread 129 (shown in FIG. 7c), therefore to keep the urine in hygienic conditions.

As shown in FIG. 7a, during the pre-diagnostic stage the urine is contained within the main compartment 111 and within the temporary compartment 126. Valve 141 seals the passage of urine from the temporary compartment 126 to the diagnostic compartment 112 through opening 142. Catch 127 in its "pre-diagnostic" stage prevents the sliding of the upper portion downward with respect to the lower portion 180. In order to initiate the diagnostic procedure, the assistant first rotates 90° the catch 127 to its "diagnostic" state as shown in FIG. 7b. Then, he pushes the lid 116 (and in fact also the upper portion 170) downwards to the "diagnostic" position as shown in FIG. 7b, namely a position where stopper 143 of the upper portion 170 engages the upper face 144 of the lower portion 180. The transfer of the device from its pre-diagnostic state (as shown in FIG. 7a) to its diagnostic state (as shown in FIG. 7b) in fact opens the opening 142 for a flow of urine, and seals the opening 145 between the main compartment 111 and the temporary compartment 126. Therefore, on one hand the content of the temporary compartment 126 flows to within the diagnostic compartment 112, and on the other hand, the full content of the main compartment is maintained within the main compartment (as it can no longer flow to within the temporary compartment 126). The limited amount of the urine in the temporary compartment, which now spills to within the diagnostic compartment 112 is sufficient for the affecting the diagnostic strip (whether it is vertical or horizontal). The diagnostic compartment 180 further comprises at its bottom a flow regulator 113 such as a small-diameter opening, a filter, an open cells sponge or a float which limits the rate of flow of the urine to within a bottom compartment 181. More specifically, the flow regulator in fact causes the strip (not shown) to be in contact with the urine for a limited period of about 3 to 7 seconds, and by the end of this period the urine is fully removed from contact with the strip allowing the strip to dry and provide indication, as the urine which was previously contained within the temporary compartment 112 is now fully contained within the bottom compartment 181. On the other hand, the main portion of the urine remains within the upper compartment 170, for a possible future use, for example, when external diagnostics become necessary.

Figure 7D:
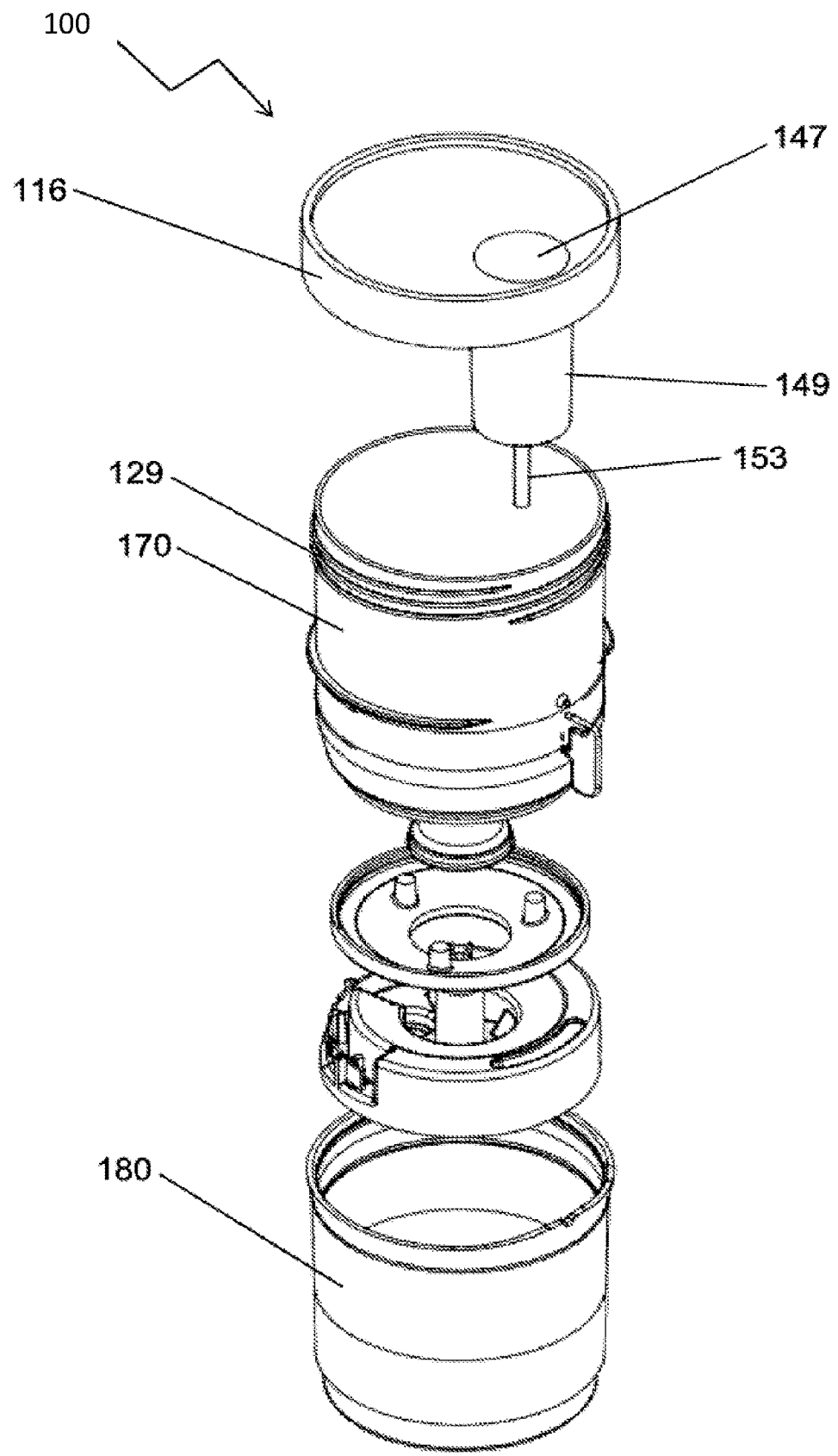

FIG. 7d shows an exploded view of the device of the invention. As can be seen, the lid 116 is attached to the upper portion by means of thread 129. The lid further comprises an opening 147 and cylinder 149 and tube 153 leading to the main compartment, for use in conjunction with an Evacuated Urine Test Tube commonly known in the art (For example, Vacutainer urine type, Urine Vacuum Test Tube—see http://www.bd.com/vacutainer/products/urine/) which pumps urine from the main compartment 111, in a hygienic manner. As seen in FIG. 7a, a needle 154 which is originally covered by a rubber sleeve is in fluid communication with tube 153, and in fact also with main compartment 111. However, originally a flow of urine within tube 153 and needle 154 into cylinder 149 is eliminated by means of said rubber cover. Only when a further examination becomes necessary, the Evacuated Urine Test Tube causes a stab of the rubber sleeve, thereby it collects urine from compartment 111 via tube 153 and needle 154 into the test tube Evacuated Urine Test Tube for further examination.

While some embodiments of the invention have been described by way of illustration, it will be apparent that the invention can be carried out with many modifications variations and adaptations, and with the use of numerous equivalents or alternative solutions that are within the scope of persons skilled in the art, without departing from the spirit of the invention or exceeding the scope of the claims.

The invention claimed is:

1. A device for diagnosing body liquids, which comprises:
   a) an upper housing and a lower housing, wherein said upper housing is vertically slidable toward said lower housing;
   b) an upper main compartment suitable to collect a fluid;
   c) a temporary compartment;
   d) a lower diagnostic compartment comprising one or more horizontally positioned diagnostic strips;
   e) a valve suitable to seal fluid connection between the temporary compartment and the lower diagnostic compartment, before a diagnostic stage is initiated, and between the temporary compartment and the upper main compartment, when a diagnostic stage is initiated; and
   f) a bottom compartment disposed below said lower diagnostic compartment, wherein one or more openings or passages between the lower diagnostic compartment and the bottom compartment which allow removal of the body liquid from the lower diagnostic compartment to the bottom compartment after flushing the total length of the diagnostic strip with said body liquid, wherein removal of the body liquid from the diagnostic compartment allows said strip to become dry and effective for visual inspection of color alterations.

2. The device according to claim 1, wherein the body liquid is urine.

3. The device according to claim 1, wherein the wall of said lower compartment is at least partially transparent, thereby to allow visual inspection of color alterations within the diagnostic strip.

4. The device according to claim 1, wherein said diagnostic strip comprises one or more sections, each being coated by a different material layer respectively, and each said layers reacts differently to a specific material or composition of the body liquid, respectively.

5. The device according to claim 1, wherein the flow of the body liquid into the lower compartment is caused as a result of a gravitational force.

6. The device according to claim 1, wherein a dosage volume in the temporary compartment is pre-determined by an opening dimension or opening period of the flow between the upper main compartment and the temporary compartment.

7. The device according to claim 1, wherein a portion of the lower diagnostic compartment is partially flat, to facilitate reading of the diagnostic strip by means of a scanner.

8. The device according to claim 1, further comprising means at the upper compartment for removing a body liquid dosage into an Evacuated Test Tube or to another test device, without opening a cover of the device.

9. The device according to claim 1, wherein the temporary compartment is suitable to hold an amount of liquid sufficient to affect the diagnostic strip.

* * * * *